United States Patent
Saraf et al.

(10) Patent No.: US 7,826,060 B2
(45) Date of Patent: Nov. 2, 2010

(54) DIRECT DETECTION OF LOCALIZED MODULATION OF ION CONCENTRATION ON AN ELECTRODE-ELECTROLYTE INTERFACE

(75) Inventors: Ravi Saraf, Lincoln, NE (US); Gaurav Singh, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 325 days.

(21) Appl. No.: 12/131,647

(22) Filed: Jun. 2, 2008

(65) Prior Publication Data
US 2009/0316157 A1 Dec. 24, 2009

Related U.S. Application Data

(60) Provisional application No. 60/941,617, filed on Jun. 1, 2007.

(51) Int. Cl.
G01B 9/02 (2006.01)
(52) U.S. Cl. .................................................. 356/450
(58) Field of Classification Search ................. 356/450, 356/517
See application file for complete search history.

(56) References Cited

U.S. PATENT DOCUMENTS

| | | | | |
|---|---|---|---|---|
| 6,052,185 | A * | 4/2000 | Banet et al. ................. | 356/450 |
| 6,803,777 | B2 * | 10/2004 | Pfaff et al. ................... | 324/752 |
| 6,812,045 | B1 * | 11/2004 | Nikoonahad et al. .......... | 438/14 |
| 7,141,429 | B2 * | 11/2006 | Munson et al. ............... | 436/53 |

OTHER PUBLICATIONS

Denpo, K. et al. "Measurement of Concentration Profiles of Cu2+ Ion and H+ Ion near a Plane Vertical Cathode by Two-Wavelength Holographic Interferometry." J. Electrochem. Soc., vol. 132, Issue 5, 1985, pp. 1145-1150.*

Singh and Saraf, "Direct Measurement of Ion Accumulation at the Electrode Electrolyte Interface under an Oscillatory Electric Field," *J Phys Chem B*, 2006, 110(25):12581-12587.

Maria Diaz-Gonzalez, et al. Recent Advances in Electrochemical Enzyme Immunoassays 2005 Electroanalysis. vol. 17 (No. 21), p. 1901-1918.

Lance S. Kuhn Biosensors: Blockbuster or Bomb? Electrochemical Biosensors for Diabetes Monitoring 1998 Interface. p. 26-31.

Chunhai Fan, et al. Electrochemical interrogation of conformational changes as a reagentless method for the sequence-specific detection of DNA 2003 PNAS. vol. 100 (No. 16), p. 9134-9137.

Yi Xiao, et al. Label-Free Electronic Detection of Thrombin in Blood Serum by Using an Aptamer-Based Sensor 2005 Angew. Chem. Int. Ed. 44, p. 5456-5459.

Eric Bakker, et al. Electrochemical Sensors 2006 Analytical Chemistry. vol. 78 (No. 12), p. 3965-3983.

Kagan Kerman, et al. Recent trends in electrochemical DNA biosensor technology 2004 Measurement Science and Technology. vol. 15, p. R1-R11.

* cited by examiner

*Primary Examiner*—Michael A Lyons
(74) *Attorney, Agent, or Firm*—Fish & Richardson P.C.

(57) ABSTRACT

The present invention directly measures localized electrochemical processes on a planar electrode using differential interferometry. The ionic charge accumulation at the electrode-electrolyte interface may be directly measured by using differential interferometry as a function of magnitude and frequency (for example, 2-50 kHz) of an external potential applied on an electrode. Methods in accordance with the present invention probe the ion dynamics confined to the electrical double layer. An electric field is applied using a pure AC potential and a superposition of AC and DC-ramp potential to measure ion concentration and detect redox processes.

18 Claims, 13 Drawing Sheets

DIRECT DETECTION OF LOCALIZED MODULATION OF ION CONCENTRATION ON AN ELECTRODE-ELECTROLYTE INTERFACE

CROSS-REFERENCE TO RELATED APPLICATIONS

This application claims priority under 35 U.S.C. §119(e) from Provisional U.S. Application No. 60/941,617 filed on Jun. 1, 2007.

STATEMENT REGARDING FEDERALLY SPONSORED RESEARCH OR DEVELOPMENT

We acknowledge the financial support of the Office of Naval Research (grant N00014-01-1-0977).

TECHNICAL FIELD

The present invention relates to the measurement of ion accumulation. More particularly, the present invention relates to measuring the accumulation of ions at a an electrode-electrolyte interface using differential interferometry as a function of the magnitude and frequency of an external electrical field. Furthermore, the method allows measurement of ion accumulation and electrochemical processes at localized places on the electrode using interferometry.

SUMMARY

The present invention provides systems and methods to directly measure the ionic charge accumulation and/or electrochemical processes at the electrode-electrolyte interface of an electrode due to applied voltage differentials. For example, an AC field or a combination of AC with DC-ramp may be applied on an electrode. Ion accumulation may be measured using high sensitivity differential interferometry. Because variations in ion concentration can alter the refractive index of an electrolyte, the ion concentration modulation due to the applied potential may be measured as a modulation of refractive index at the electrode-electrolyte interface. Because the modulation is only recorded at the spot where a light beam used for the interferometry is incident on the electrode, the measured ion modulation is localized to that spot. The light beam used for interferometry may be a laser beam. Further, a the laser beam may be scanned over various spots on an electrode to independently measure ion modulation activity from spot to spot on the electrode. In this fashion different materials may be placed at different spots on an electrode and the properties of those materials, as manifested by varying ion modulations, may be measured. The ion modulation depends both on non-Faradic processes which are due to simple Coulombic attraction or repulsion between the ion and the electrode, or Faradic processes where an electron transfer between the ion and the electrode occur constituting a reduction or an oxidation reaction. Signatures of both Faradic and non-Faradic processes may be recorded using systems and/or methods such as described herein.

BRIEF DESCRIPTION OF THE SEVERAL VIEWS OF THE DRAWINGS

Illustrative embodiments of the present invention are described in detail below with reference to the attached drawing figures, which are incorporated by reference herein and wherein.

DETAILED DESCRIPTION

Figure 1:
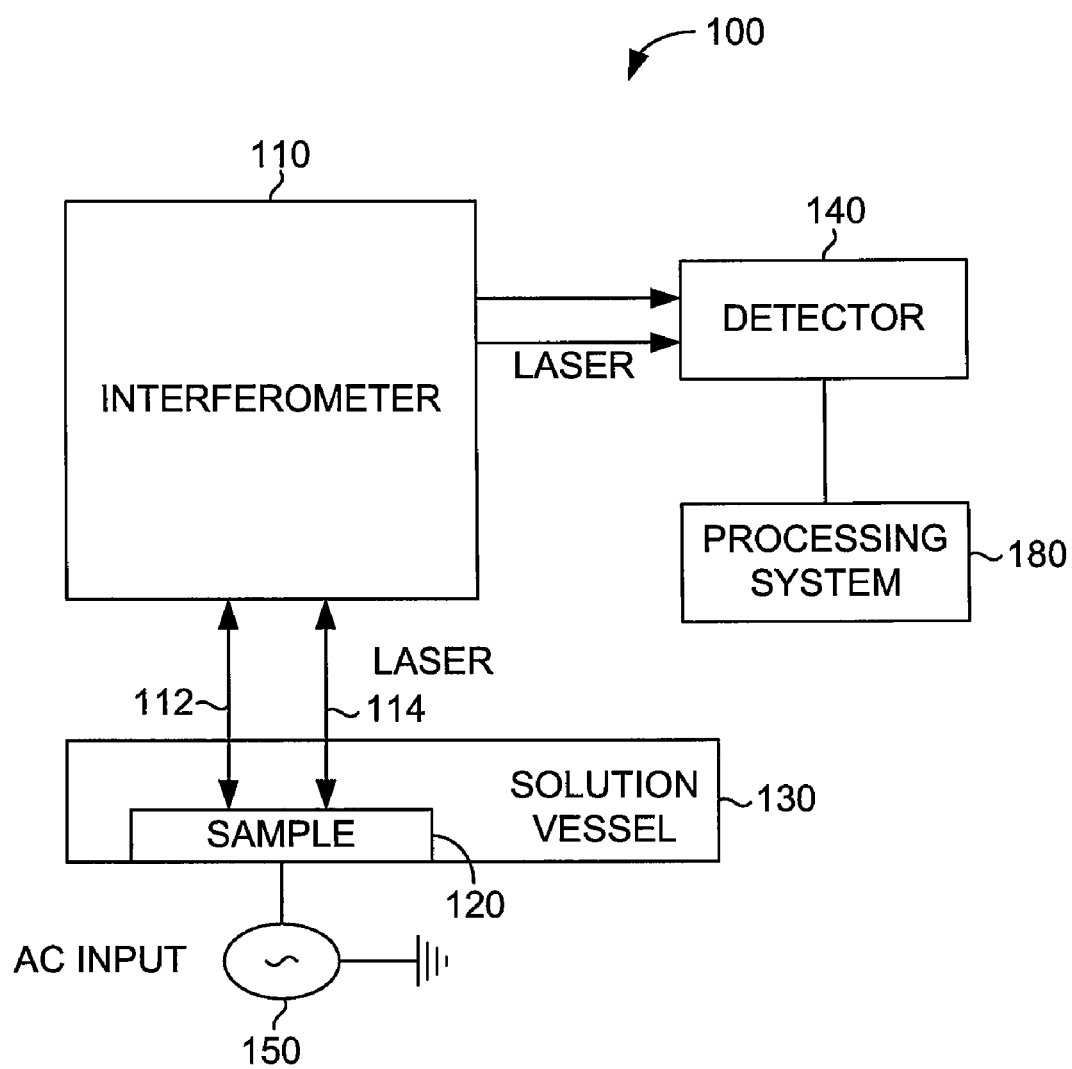
FIG. 1 illustrates an example interferometer system in accordance with the present invention.

An article entitled "Direct Measurement of Ion Accumulation at the Electrode Electrolyte Interface under an Oscillatory Electric Field," by Gaurav Singh and Ravi F. Saraf published in the Journal of Physical Chemistry on Jun. 3, 2006 is hereby incorporated by reference.

Manipulation of electrolyte and polyelectrolyte (such as DNA, proteins) solutions, and suspension of biological systems (such as cells) in water by an oscillatory (i.e., AC) electric field has become of great interest in the recent years, spurred by the need to design microfluidic and nanofluidic systems for various biomedical devices to reduce sample volumes and analysis time. AC fields in such micro-fluidic systems can manipulate, separate, and trap DNA and protein molecules; self-assemble and manipulate colloid particles; separate and manipulate cells and vesicles; analyze DNA hybridization for gene sequencing; and pump and manipulate electrolyte solutions in fluidic channels. Due to the high surface-to-volume ratio of these devices, understanding the dynamics of ion motion at the electrode-electrolyte interface is central to the performance of these electro-kinetic-fluidic systems.

An Electrical Double Layer (EDL) is formed at the solution/electrode interface because of the electrostatic interaction between the ions in the solution and the electrode surface. The result is an ion-concentration gradient that typically extends from Angstroms to tens of nanometers into the bulk solution depending on the ionic strength of the aqueous solution. Because most of the interfacial charge is screened within the double layer, the thickness of the EDL is also the length scale of interaction between charged moieties in electrolyte solution. For a simple salt solution, the thickness of EDL is given by the Debye length, $\zeta = [\epsilon_r \epsilon_0 kT/(\Sigma N_A c_{\infty,i} e^2 z_i^2)]^{0.5}$, where $\epsilon_0$ is permittivity in a vacuum, $\epsilon_r$ is the dielectric constant of the liquid (i.e., water), $N_A$ is Avogadro's number, kT is thermal energy, $c_{\infty,i}$ is the (bulk) molar concentration of the ith ion and $z_i$ is its valency, and e is the charge of the electron. Typically, for NaCl in water, $\xi = 0.303/[NaCl]^{0.5}$ nm, where [NaCl] is the molar concentration.

The theory for the static structure of EDL (i.e., ion distribution at the interface) under constant (or zero) bias between electrodes is a two-layer structure comprised of a relatively immobile, densely packed Stern layer and a diffuse ionic layer with high mobility. Although equivalent RC-circuit models, where R is bulk resistance and C is the interfacial capacitance, for the metal-electrolyte interface have been established for over a century, their applicability has been questioned at a fundamental level over the years. Furthermore, the relevant time scale is a geometric mean of the characteristic relaxation time of the ion-dynamics in the bulk and the EDL that are difficult to decouple. Thus, the need for a direct experimental approach that exclusively measures the ion accumulation at the electrode-electrolyte interface under AC-field polarization is acutely felt.

The present invention provides systems and methods to directly measure modulation of ion concentration at the electrode-electrolyte interface upon application of a time dependent electric potential on the electrode. Differential interferometry may be used in accordance with the present invention to directly measure the ionic charge accumulation at the electrode-electrolyte interface as a function of the magnitude and frequency (for example, 2-50 KHz) of an external potential applied on the electrode. One exemplary embodiment described herein uses pure AC to measure ion dynamics. Another exemplary embodiment described herein uses a superposition of AC and a DC-ramp potential to measure ion dynamics and detect a Faradic process (i.e., redox reaction) at the electrode-electrolyte interface. In this embodiment, the DC-ramp potential may be a "saw-tooth" potential where the potential increases linearly from a first potential ($V_1$) to a second potential ($V_2$) and then drops rapidly back to $V_1$. Typically the frequency of the DC-ramp will be at least one thousand times slower, preferably ten thousand times slower, than the AC potential.

The miniaturization of systems, primarily fueled by Si fabrication, has led to a class of analytical method usually referred to as "combinatorial analysis". In combinatorial analysis, tens to thousands of analytical functions can be performed on a single monolithic surface, such as a Si chip. The present invention provides powerful systems and methods to measure enzymetic binding, DNA bind, protein binding, and many other chemical bindings. Localized electrochemical processes on different spots of the same electrode may be measured as described herein to allow for combinatorial analysis. For example, a planar surface of the working electrode may have different DNA sequences in different spots, potentially including one or more unknown DNA sequences. The working and reference electrodes may then be exposed to a DNA sequence in the solution. Fragments of the DNA sequence from the solution will preferentially adhere to fragments of its complementary DNA sequence on the working electrode. Because DNA is negatively charged, a spot that has more DNA fragments will be more negatively charged, causing a different modulation of ions than in spots with fewer DNA fragments. The absolute concentration may then be measured at each spot on the working electrode by measuring the differences in refractive index, which is dependent on the differences in ionic concentration for a given spot in the matrix. In another embodiment, an array of approximately 100 micron diameter spots of single stranded DNA oligomer of known sequence on a chip may be immobilized by exposing the array to a sample solution that contains a mixture of single strand DNA with unknown sequences. Depending on the base complimentarity, based on which spots bind to the fragments of DNA in the sample, the sequence of hundreds of different DNA fragments in the solution may be obtained simultaneously.

FIG. 1 illustrates an example of a general interferometer system 100 in accordance with the present invention. The system 100 utilizes interferometry to measure the modulation of ions at the interface between an electrode and electrolyte. Differing concentrations of ions within localized regions of a solution can result in those localized regions exhibiting differing refractive indexes. The differing refractive indexes result in different path lengths for light traversing those regions, which can be detected and quantified using interferometry. The system 100 comprises an interferometer component 110, a sample component 120, a solution vessel component 130, a detector component 140, and an AC input component 150. It will be understood by those of ordinary skill in the art that the components illustrated in FIG. 1 are exemplary in nature and in number and should not be construed as limiting. Any number and/or variety of components may be employed without departing from the scope of the present invention.

Still referring to FIG. 1, interferometer component 110 may transmit a signal laser beam 112 and a reference laser beam 114, both of which fall on sample 120 within solution vessel 130. If signal beam 112 passes through solution with a different ion modulation than the solution reference beam 114, the differing reactive index caused by the varying ion modulations will result in signal beam 112 and reference bean 114 traveling paths of different lengths. If signal beam 112 and reference beam 114 travel paths of different lengths the beams will be out of phase when superimposed after reflection. Sample 120 may comprise at least two electrodes. For example, sample 120 may comprise a reference electrode upon which reference beam 114 is incident and a working electrode upon which signal beam 112 is incident. In such an arrangement, the composition of reference electrode and working electrode may differ, which can result in differing ion modulation near the working electrode relative to the reference electrode and, therefore, different refraction and a different path length for signal beam 112 relative to reference beam 114. Reference beam 114 and signal beam 112 are reflected by sample 120 (for example, by reference electrode and working electrode). The reflected beams (including signal beam 112 and reference beam 114) are superimposed in interferometer 110 to measure any phase difference between the reflected beams, which corresponds to differences in the modulation of ion concentration due to an externally applied electric field. Sample 120 may comprise, for example, a set of two Au electrodes on a thin film deposited on a $SiO_2$ passivated Si chip. If desired, a sample for use in testing (such as DNA, protein, an alloy, etc.) may be placed on all or part of the surface of one electrode. The two electrodes may be spaced about 20 μm apart. Typically, the small dimension of each electrode may be about 1 mm and the thickness may be about 300 nm. To improve adhesion of the electrodes to the $SiO_2$ passivated Si chip, an adhesion layer of Cr, Ti, or W may be used. The adhesion layer may be less than or equal to 10 nm. One of skill in the art will understand that the spacing between the electrodes will depend on the distance between signal laser beam 112 and reference laser beam 114. All dimensions described herein are exemplary and may be altered as per design without changing the essential principle of the invention.

Figure 2:
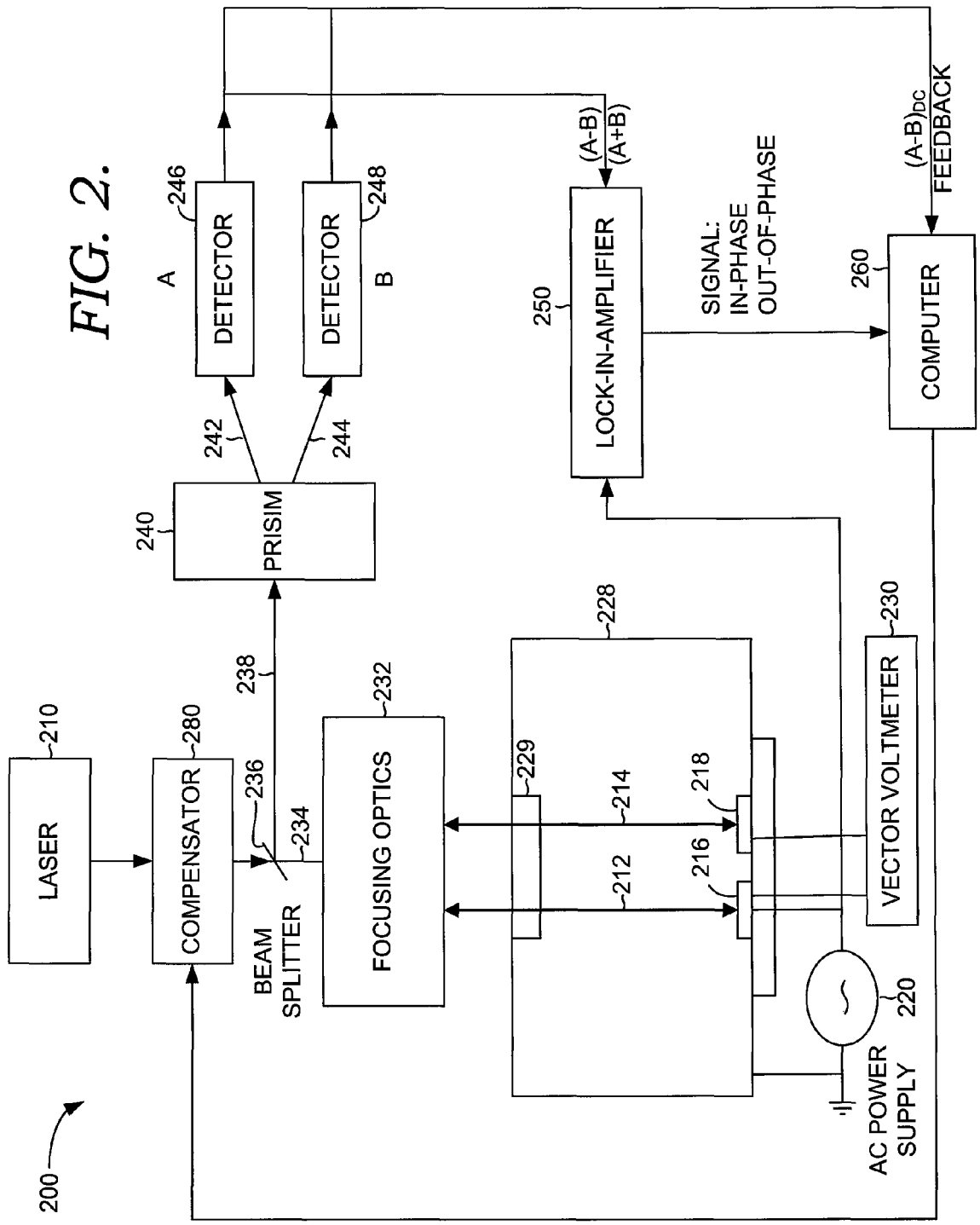
FIG. 2 illustrates a further example system in accordance with the present invention.

Referring to FIG. 2, a further example of a system 200 in accordance with the present invention is illustrated. System 200 may include, among other components, laser 210, a first electrode 216, a second electrode 218, AC Power supply 220, solution vessel 228, vector voltmeter 230, optical device 240, a first detector 246, a second detector 248, and lock-in amplifier 250. Laser 210 may comprise a He/Ne laser. Laser 210 may emit a laser beam 234. Laser beam 234 from laser 210 may be split into two orthogonally polarized beams in beam displacer focusing optics 232, producing signal laser beam 212 and reference laser beam 214, where signal laser beam 212 and reference laser beam 214 are approximately 60 μm apart with equal intensities but mutually perpendicular linear polarization. Signal laser beam 212 and reference laser beam 214 will be in phase as they depart displacer focusing optics 232. First electrode 216 and second electrode 218 may comprise for example, Au electrodes with a sample for investigation present on first electrode 216 where signal laser beam 212 is incident. Solution vessel 228 is grounded and may comprise a Au plated Ti chamber. Vessel 228 may include one or more optical window 229 to permit beams to enter and/or exit vessel 228. Optical device 240 may comprise a Wollaston prism. Focusing optics 232 may alternatively comprise a biaxial crystal. Detectors 246 and 248 may comprise amplifiers and may be photodetectors. AC Power supply 220 may be a battery.

As shown in FIG. 2, signal laser beam 212 is incident on first electrode 216 and reference laser beam 214 is incident on second electrode 218 surfaces of working respectively. First electrode 216 may also be referred to as working electrode, and second electrode 218 may also be referred to as reference electrode. Further, working electrode 216, as well as reference electrode 218 if desired, may be divided into a plurality of spots, such that the laser beam is incident upon a given spot of the plurality at a given time. In an exemplary embodiment, the plurality of spots may be a matrix of spots. Each spot may have a size of, for example, 20 μm by 20 μm. Different samples for testing may be applied to different spots on an electrode. This approach permits, for example, the testing of a plurality of samples substantially simultaneously. For example, signal laser beam 212 may sequentially "read" each of a plurality of spots on working electrode 216 to measure the localized ion modulation at each spot relative to the localized ion modulation at the reference electrode 218. Working electrode 216 may be connected to AC power supply 220 at a frequency, ω. Reference electrode 218, may be floating or grounded. Vector voltmeter 230 measures the potential and phase of reference electrode 218 with respect to working electrode 216. The reflected beams (including signal laser beam 212 and reference laser beam 214) are superimposed in focusing optics 232. Optical device 240 separates polarized laser beams into two outgoing beams 242, 244. First detector 246 and second detector 248 measure the relative phase of beams 242 and 244, which modulates as a result of the ion modulation. The output of first detector may be designated A, and the output of second detector may be designated B. Lock-in amplifier 250 measures the AC component of A–B with respect to external applied potential, wherein the AC component is the signal due to the path length modulation caused by ion motion. Typically, three signals may be measured: two time independent (i.e., DC) signals from an amplifier connected to each detector, 246 and 248; and the amplitude of the modulating A–B signal from lock-in amplifier 250, which is tuned to measure a signal at frequencies that are a multiple of the applied AC potential on the electrode. One of skill in the art will appreciate that ambient light, which usually flickers at a frequency of less than 100 Hz, may be used because lock-in amplifier 250 may filter the signal in KHz frequency.

Typically, DC signals A and B measured from detectors 246 and 248 respectively and the A–B signal measured from lock-in amplifier 250 may be fed into computer 260 with a data acquisition card to obtain the amplitude of the A–B signal and the total intensity A+B, which is constant and corresponds to the total light intensity of laser 210. The total intensity A+B may be measured to "normalize" the signal with respect to the total beam intensity that changes due to thermal noise in laser 210 and optical components 232 and 240. A feedback loop with compensator 280 may be utilized to maintain the DC component of the $(A-B)_{DC}$ signal, wherein the DC component will fluctuate due to thermal drifts from optical components 232 and 240. One of skill in the art will understand that the feedback will reduce noise and maintain the interferometer at high sensitivity. Additionally, one of skill in the art will understand that the optic axis of beam displacer focusing optics 232 and optical device 240 may be optimized for high sensitivity, which may be accomplished by placing compensator 280 in the beam path after laser 210.

Referring again to FIG. 2, in one exemplary embodiment the amplitude of path length modulation, Δ, due to motion of the ions caused by applied external pure AC field on an electrode may be measured using a differential interferometer. Due to the external AC field, the ion accumulation in the interfacial region of the electrodes will modulate. The ionic charge modulation will cause refractive index modulation in the beam path in the two laser beams 212 and 214. The path length change in signal laser beam 212 on working electrode 216 relative to reference beam 214 may be estimated from the signals measured at detectors A and B, 246 and 248 respectively, and lock-in amplifier 250. From the three signals A, B (measured from detectors 246 and 248), and A–B (measured form lock-in amplifier 250), computer 260 will obtain $(A+B)_{DC}$, $(A-B)_{DC}$, and $(A-B)_{AC}$. The amplitude of path length modulation in signal beam 212 on working electrode 216 relative to reference beam 214, Δ, is $[(A-B)_{AC}/(A+B)_{DC}](\lambda/4\pi)$, where $(A+B)_{DC}$ is nominally a constant that is proportional to the total laser intensity and λ is the wavelength of the laser. Thus, Δ is directly estimated from measured signals without manipulation or fitting.

With continued reference to FIG. 2, the measured modulation, A, is modified due to concomitant modulation in reference beam 214. To obtain ion dynamics using the above approach, the absolute modulation of the ion accumulation at working electrode 216 needs to be determined as if reference electrode 218 were at zero potential (i.e., ground). For high sensitivity (i.e., path length difference of $<10^{-3}$ nm) the two beams (signal beam 212 and reference beam 214) need to pass through a similar environment to reduce differential phase fluctuations from thermal noise, and to have equal intensities during interference they must reflect from similar surfaces. In an exemplary embodiment, a similar environment is created by passing the beams close and parallel to each other. Further, the reflective surfaces may be Au electrodes. One of skill in the art will appreciate that sample materials applied to one or more electrode may impact the reflectivity encountered by signal beam 212 relative to the reflectivity encountered by reference beam 214. One of skill in the art will appreciate that such relative differences in reflectivity could impact measurements and, further, that any such relative differences may be reduced/eliminated by modifying the surfaces of one or both electrodes and/or electronically or computationally compensating for reflectivity differences in the resulting signals. One of skill in the art will understand that due to the close proximity of electrodes 216 and 218, live electrode 216 connected to AC power supply 220 may induce a potential on the adjacent reference electrode 218 upon which reference laser beam 214 is incident. As a result, both the signal and reference laser beams, 212 and 214 respectively, will modulate at multiples of the frequency ω. Accordingly, an independent measurement using vector voltmeter 230 may be performed to measure the relative phase and amplitude between reference electrode 218 and working electrode 216.

Referring again to FIG. 2, the phase difference between reference electrode 218 and working electrode 216, φ, may be measured by vector voltmeter 230. The electrical characteristics of $V_L$, $V_R$, and φ are as follows: (i) for all salt conditions, φ decreases from a maximum of approximately 18 degrees at ω<10 kHz toward 0 degrees as the frequency increases; (ii)

the working and reference electrode are in-phase for ω>40 kHz for all the salt concentrations where φ is approximately 0 degrees, implying true potential $V_T=V_L-V_R$; (iii) the percent decrease in voltage, $R=(V_L-V_R)/V_L$, decreases monotonically with increasing ω; (iv) R is within 40% to 70% for the frequency range tested; (v) At fixed ω, φ is constant at all $V_L$ (within 1 degree) and $V_R$ is perfectly linear with respect to $V_L$ for all the salt concentrations, applied potentials, and frequencies.

The absolute modulation of ions, $\Delta_A$, exclusively on working electrode 216, upon which signal laser beam 214 is incident, may be estimated from the measured amplitude of path length modulation Δ. For an amplitude of applied potential $V_L$ on working electrode 216 and a frequency ω, reference electrode 218 will have an amplitude of induced potential $V_R$. The mobility of ions has a finite speed and will experience friction from the solvent molecule during motion. As a result, there is a phase difference, φ, between reference electrode 218 and working electrode 216 which can be directly measured by vector voltmeter 230. By assuming the applied voltage, $V_L$, at a phase of 0 degrees, the in-phase, $\Delta_0$, and out-of-phase, $\Delta_{90}$, amplitude of absolute modulation at true potential, $V_T=V_L-V_R \cos \phi$, of working electrode 216 with respect to reference electrode 218 is given by:

$$\Delta_0 = \frac{\Delta[a\sin\theta - \cos\theta]}{[a^2 - 1]} \qquad \text{(Equation 1a)}$$

$$\Delta_{90} = \frac{\Delta[a\cos\theta - \sin\theta]}{[a^2 - 1]} \qquad \text{(Equation 1b)}$$

Where $\alpha=V_R \sin \phi[V_L-V_R \cos \phi]$ and θ is the measured phase angle of $(A-B)_{AC}$ with respect to applied voltage determined by lock-in amplifier 250. Thus, the absolute modulation, $\Delta_A=[\Delta_0^2+\Delta_{90}^2]^{0.5}$ and the phase of the absolute modulation with respect to $V_T$ is given by $\theta_A=\tan^{-1}(\Delta_{90}/\Delta_0)$.

The amplitude of ion concentration modulation can be obtained, by Snell's law, from $\Delta_A$ as a function of true applied voltage, $V_T$ by:

$$\Delta_A = \int_0^h \left\{ \left(\frac{dn}{dc}\right)_- c_-(x) + \left(\frac{dn}{dc}\right)_+ c_+(x) \right\} dx \approx \qquad \text{(Equation 2)}$$
$$\left(\frac{dn}{dc}\right)_- \int_0^h c_-(x) dx$$

In Equation 2 the subscripts + and − correspond to the property for cation and anion respectively, (dn/dc) is the differential refractive index of the ion species; $c_i(x)$ is concentration of the ion species; x is the distance from the electrode surface; and h is the nominal thickness of the electrode-electrolyte interface. The differential refractive index, (dn/dc), may be tabulated for most of the common ions and salts or may be measured using a refractometer, which is commercially available. Because $(dn/dc)_- >> (dn/dc)_+$ and $(dn/dc)_i$ is a constant for concentrations well above 5M, path length modulation is primarily due to the motion of the anion.

The refractive index modulation measured from Δ consists of ion motion in the electric double layer, which has a thickness on the order of Debye length ζ, and a diffusion layer, which has a thickness h on the order of √(D/ω), where D is the diffusion coefficient of the ions. For example, the frequency ω may be in a range of 2 to 50 kHz, leading to a thickness upper limit of 1 μm for the diffusion layer. Thus, the measured modulation of path length is confined only to the concentration modulation within approximately 1 μm from the electrode-electrolyte interface. Further, the interfacial thickness, h, is nominally in a range of approximately 2ζ to 100ζ, depending on the ion mobility and ion diffusion. In the preferred embodiment, the interfacial thickness, h, is approximately 5ζ. The average ion modulation in the interfacial layer of the cation due to the applied external AC field is given by:

$$\delta_- = \frac{1}{h} \int_0^h c_-(x) dx \qquad \text{(Equation 3a)}$$

In the preferred embodiment, the interfacial thickness, h, is approximately 5ζ. Using Equation 3a and a nominal h of 5ζ, the average ion modulation from the measured modulation of path length is given by:

$$\delta_- = \Delta_A \left[\left(\frac{dn}{dc}\right)_- 5\zeta\right]^{-1} \qquad \text{(Equation 3b)}$$

Figure 3:
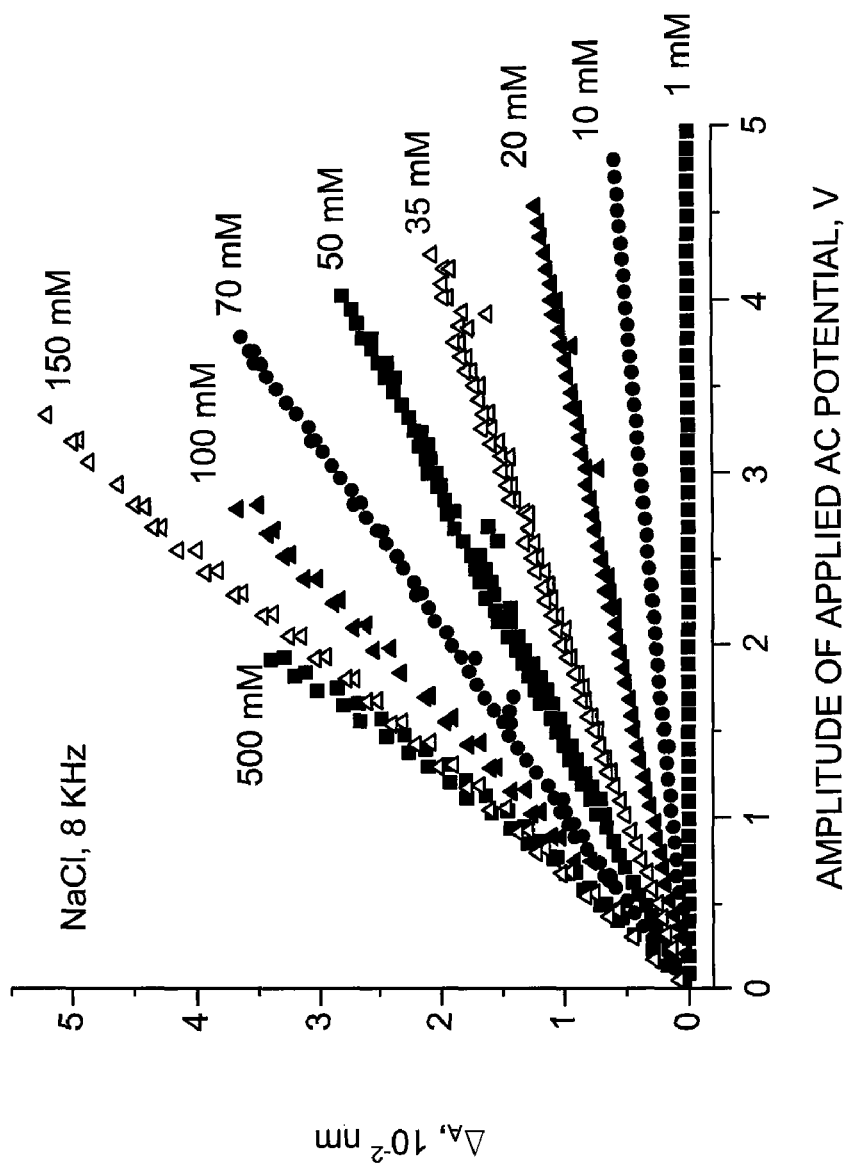
FIGS. 3 through 7 show measurements taken using interferometric systems and/or methods in accordance with the present invention.

An exemplary embodiment of system 200 as shown in FIG. 2, uses a pure AC potential to measure ion accumulation for a non-Faradic process (where the ions do not exhibit redox), the results of which are illustrated in FIG. 3. An aqueous solution of NaCl in solution vessel 228 is exposed to electrodes 216 and 218, which are Au electrodes. An AC potential at a fixed frequency, ω=8 KHz, is applied to working electrode 216 with amplitude, $V_L$, ranging from 0 to 5V. Laser 210 produces signal and reference laser beams, 212 and 214 respectively, that are incident on a spot size of approximately 10 μm and have a wavelength of approximately 633 nm. In FIG. 3, the absolute modulation, $\Delta_A$, of Cl⁻ ions is shown as a function of the amplitude of applied AC potential, V, for salt concentration ranging from 1 to 500 mM. As can be seen in FIG. 3, the absolute modulation of Cl⁻ ions is highly linear. The signal is well over the sensitivity of the interferometer, which can measure $\Delta_A$ as small as $10^{-4}$ nm. One of skill in the art will understand that using a laser emitting a beam of smaller wavelength and modified optics, will allow measurement on a spot size of about 1 μm.

Figure 4:
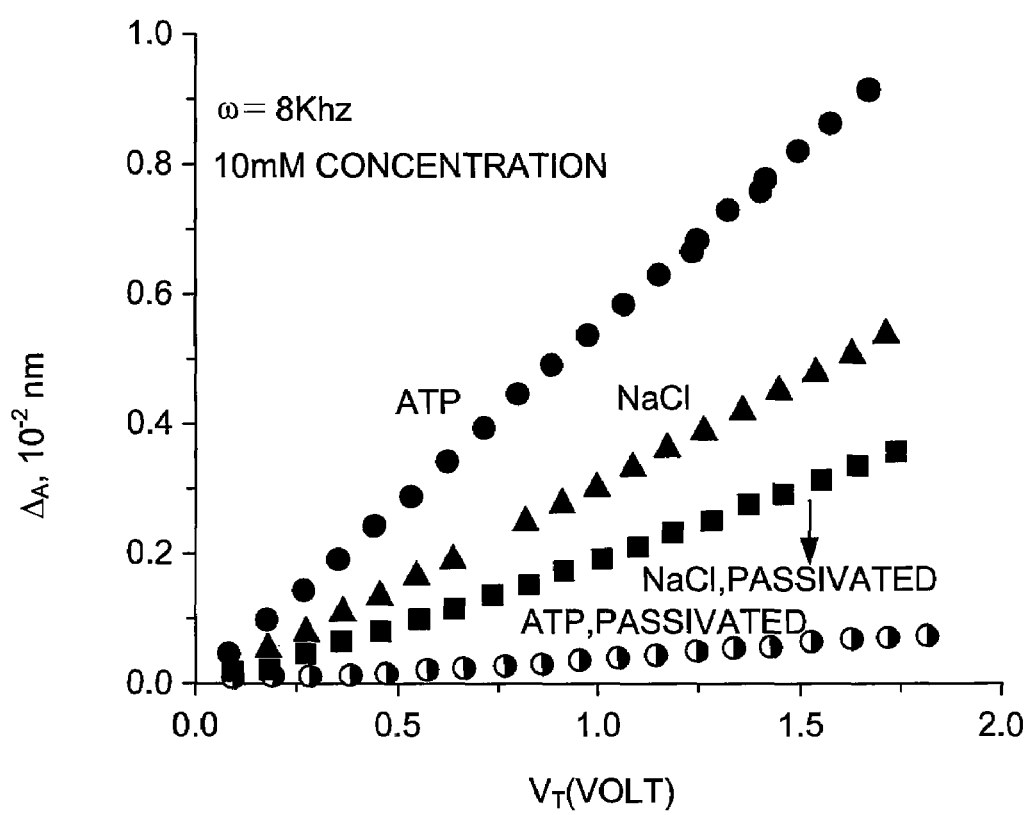

FIG. 4 compares the dynamics as measured using interferometry in accordance with the present invention of a 10 mM solution of sodium salt of adenosine triphosphate (ATP) and NaCl by plotting the absolute modulation, $\Delta_A$, as a function of true potential, $V_T$, for a passivated and plain wafer. The modulation of ATP is higher than the modulation of NaCl, and one of skill in the art can appreciate that this may be a result of the higher polarizability of ATP, even though the ion is bivalent (i.e., 50% fewer molecules are needed to compensate for the charge on the electrode). The passivated wafer may comprise a self-assembled monolayer (SAM) of octadecanethiol (ODT) with a thickness of 2 nm on the electrode surface and may be immobilized to reduce the influence of the charge on the electrode. The SAM layer may be formed by depositing ODT from a 1 mM ethanolic solution for 22 hours. FIG. 4 shows that passivation due to SAM significantly reduces the ion dynamics. The effect of passivation is significantly more dramatic for the ATP ion than for Cl⁻ ion. Given that there are no Faradic processes, it is expected that the attenuation of the field due to an approximately 2 nm thick monolayer at a distance h should be independent of an ion's size. Thus, the dynamics in the diffusion layer should attenuate by the same amount for ATP and NaCl. The significantly large discrepancy in percent attenuation for ATP and NaCl implies that the observed signal is primarily from dynamics in the EDL. One of skill in the art will appreciate that the 90% attenuation of signal for ATP compared to 50% for Cl⁻ may be attributed to the larger size of ATP that is more impeded by SAM and Cl⁻ due to size exclusion. The Cl⁻ can intercalate between the ODT chains. This reversal in trend due to passivation by a layer that is approximately 2 nm, which is comparable to the EDL thickness, indicates that the measured dynamics in the present invention is primarily due to ion dynamics in the EDL. The dynamics in the diffusion layer is not ruled out, but it has an insignificant contribution to the overall signal.

Figure 5A:
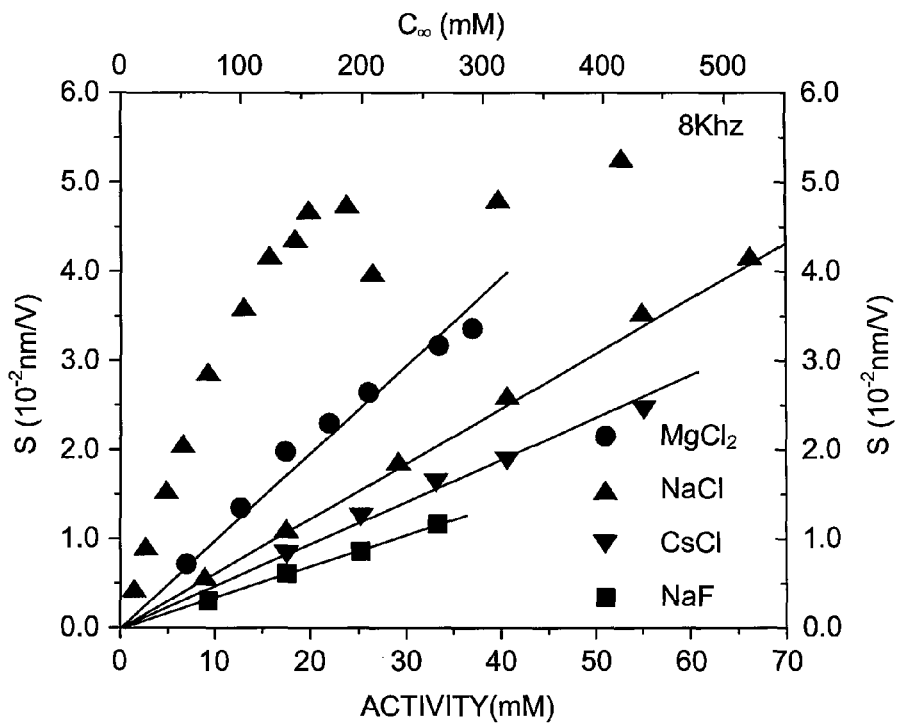
Figure 5B:
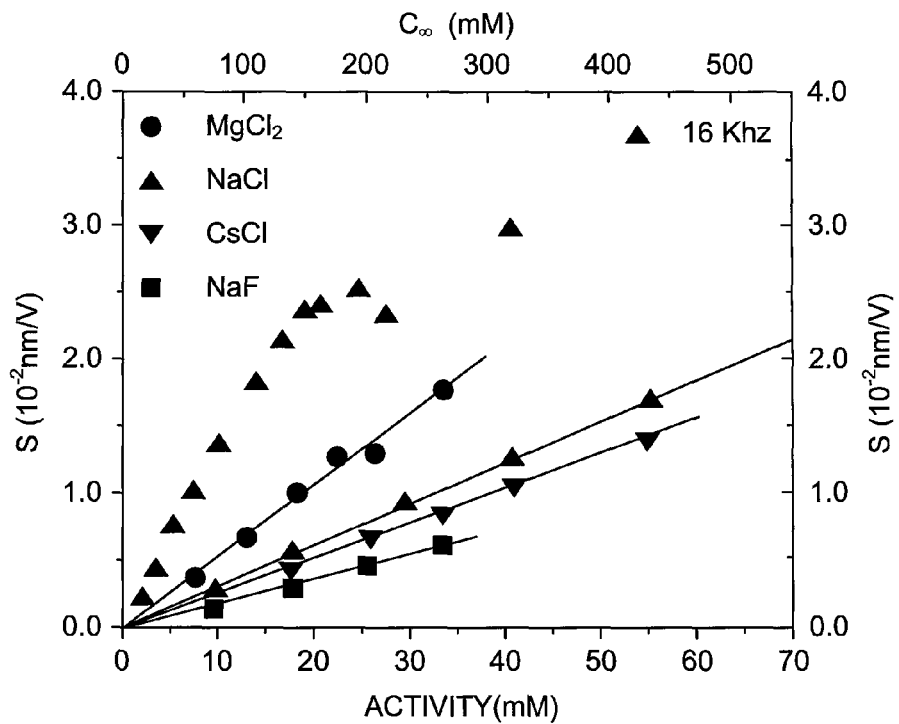

FIGS. 5A and 5B show the slope, S, of the $V_T$ versus $\Delta_A$ plot, where $\Delta_A = SV_T$, as a function of concentration for various salts. To account for exact ion strength, activity may be plotted, where activity, A, may be calculated by a standard semiempirical formula valid for <100 mM concentration. For the limited concentration range, c, is linearly proportional to the slope, S, for dynamics at fixed frequency, wherein the fixed frequency of FIG. 5A is ω=8 kHz and the fixed frequency of FIG. 5B is ω=16 kHz. The linearity for all the lines calculated from the fitness parameter is $R^2$ of 0.99 or better. The slopes of the lines in $10^{-4}$ nm/(V-mM) at a frequency of 8 kHz are 9.72, 6.07, 4.65, 3.4 for $MgCl_2$, NaCl, CsCl, and NaF, respectively and at a frequency of 16 kHz are 5.41, 3.04, 2.56, 1.83 for $MgCl_2$, NaCl, CsCl, and NaF, respectively. Some qualitative inferences may be drawn from the observations in FIGS. 5A and 5B. As stated in equation 2, the influence of the cation is negligible; therefore NaCl and CsCl should quantitatively behave similarly. The slightly smaller slope for CsCl is rationalized by the higher polarizability of $Cs^+$ compared to $Na^+$ leading to a lower contrast for Cl⁻ dynamics. Also, the slope for $MgCl_2$ is significantly larger than that for NaCl. The higher charge on $Mg^{2+}$ compared to $Na^+$ will lead to more efficient depletion of Cl⁻ during the negative cycle leading to a larger peak-to-peak modulation of the anion. Further, that the slope of NaF is lower than that of NaCl may be attributed to the larger polarizability of $Cl^{-1}$ than $F^-$. As (dn/dc) is approximately the ion size, the ratio of the slopes should be the ion size ratio of approximately 1.4. A slightly larger ratio of about 1.7 was observed. Additionally, at higher concentrations, although the linearity is maintained, the slope (S) begins to plateau, indicating a saturation effect.

Figure 6:
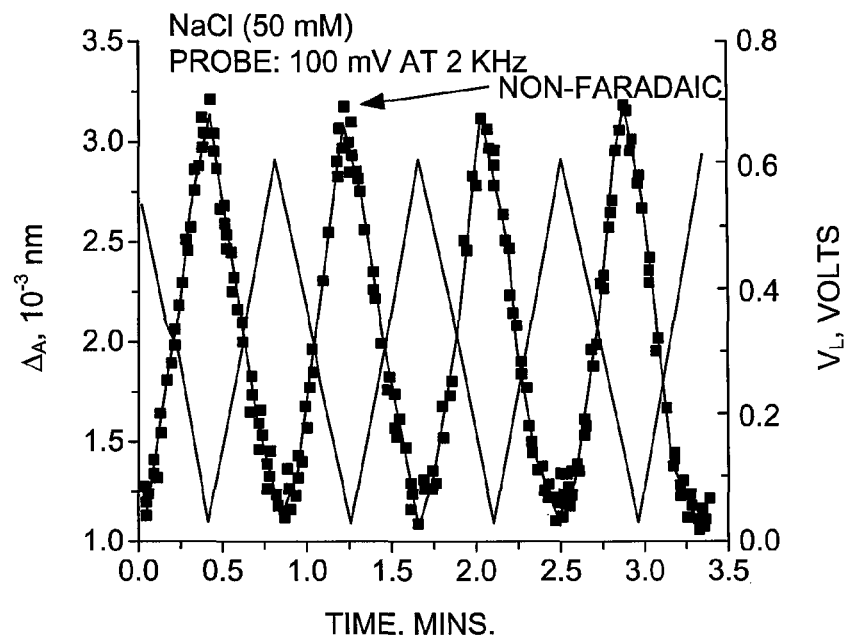

Another exemplary embodiment of system 200 as shown in FIG. 2, uses a combination of AC and DC-ramp potential to measure ion dynamics and detect Faradic process (i.e., redox reaction) at the electrode-electrolyte interface. Again, laser 210 produces signal and reference laser beams, 212 and 214 respectively, that may be incident on a spot size of approximately 10 μm and have a wavelength of approximately 633 nm. FIG. 6 shows the dynamics of chlorine ions. As depicted in FIG. 6, 50 mM NaCl in water solution was subjected to a 2 KHz AC field with a 100 mV amplitude. A ramp potential $V_L$, or saw-tooth cycle, between 0 and 0.7 volts were superimposed with the AC potential. Because the measured $\Delta_A$ as a function of ramp potential $V_L$ corresponds to the modulation caused by the AC potential, the 2 KHz AC potential is referred to as the "probe potential." FIG. 6 illustrates the change in $V_L$ and corresponding $\Delta_A$ as a function of time. The dynamics of NaCl shows that the Cl⁻ ions were most mobile to the AC field at a 0 volt ramp, and were least mobile at 0.7 volt. One of skill in the art may appreciate that this indicates charging and discharging of the double layer. At 0.7 volt, the electrical double layer was completely charged, so the potential was completely screened, leading to a low signal. This illustrates that the modulation is the highest at lowest $V_L$ for a non-Faradic process.

Figure 7:
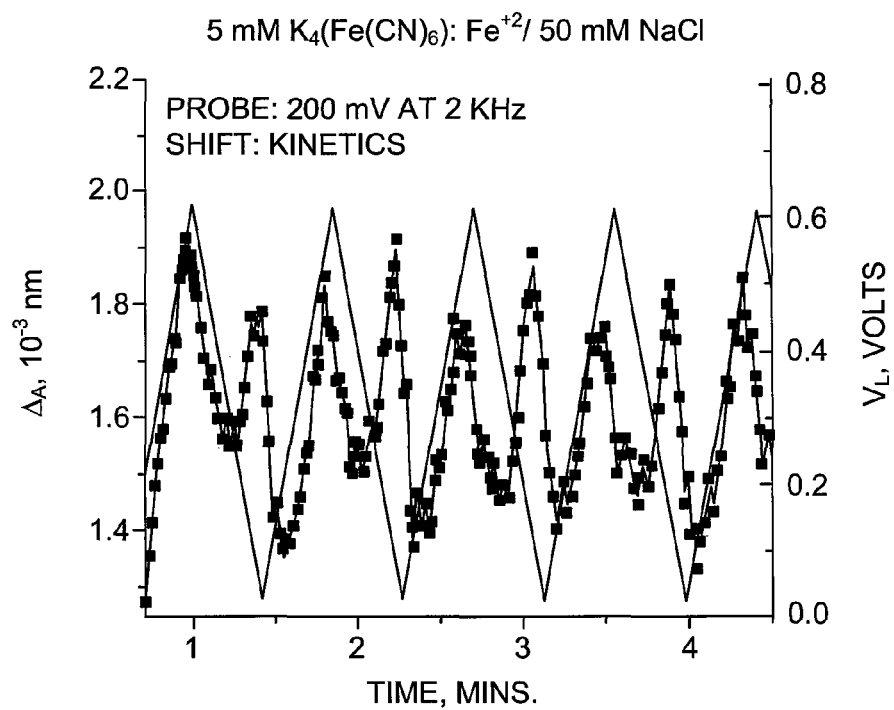

FIG. 7 illustrates measurements taken from the observation of a redox process of $Fe^{+2} \rightarrow Fe^{+3}$ + e. A combination of 50 mM NaCl and 5 mM $K[Fe(CN)_6]$ solution is subjected to the same external potential as discussed for FIG. 6. The $\Delta_A$ exhibits two maxima—one at the lowest $V_L$, similar to pure NaCl, and an additional peak close to the highest $V_L$. Oxidation of $Fe^{+2}$ is manifested as a second peak indicated in FIG. 12. As the ramp potential, $V_L$, increases, more $[Fe(CN)_6]^{4-}$ ions begin to accumulate at the electrode. Beyond a certain positive potential the electron is extracted from the ions to convert them to $[Fe(CN)_6]^{3-}$. This leads to a sudden decrease in total positive charge in the interfacial layer and causes attraction of more $[Fe(CN)_6]^{4-}$ from the bulk. As a result, the ion accumulation of the cation (and hence the net refractive index) increase causing the Faradic peak at highest $V_L$, which corresponds to the oxidation of $[Fe(CN)_6]^{4-}$. One of skill in the art will understand that if the ramp potential is increased beyond 0.7 V there will come a point that other processes such as diffusion and redox kinetics will become important causing the Faradic peak to not correspond exactly to the highest $V_L$. Analogous to cyclic voltametry, the Faradaic peak is slightly shifted from the DC maxima due to kinetic effects. It should be noted that the sensitivity illustrated is one thousand fold better than conventional techniques.

When the system is exposed to a combination of AC and DC-ramp potential, ion modulation can be measured and redox processes can be detected. In one example, differing alloys may be placed in different spots in the working electrode matrix of spots. The working electrode may be exposed to a corrosive solution. For example, the conducting solution used may itself be corrosive. After examining each spot using interferometric systems and/or methods in accordance with the present invention, a combinatorial analysis may be performed to find alloys or alloy formulations for corrosive resistance. For example, the spot that has the highest rate of chemical reaction rate may be expected to be the most susceptible to corrosion. In another embodiment, different enzymes may be placed in different spots on the working electrode and exposed to a solution with a substrate. The enzymes that best bind to the substrate may then be detected because as soon as an enzyme binds to the substrate an electron transfer occurs.

Figure 12:
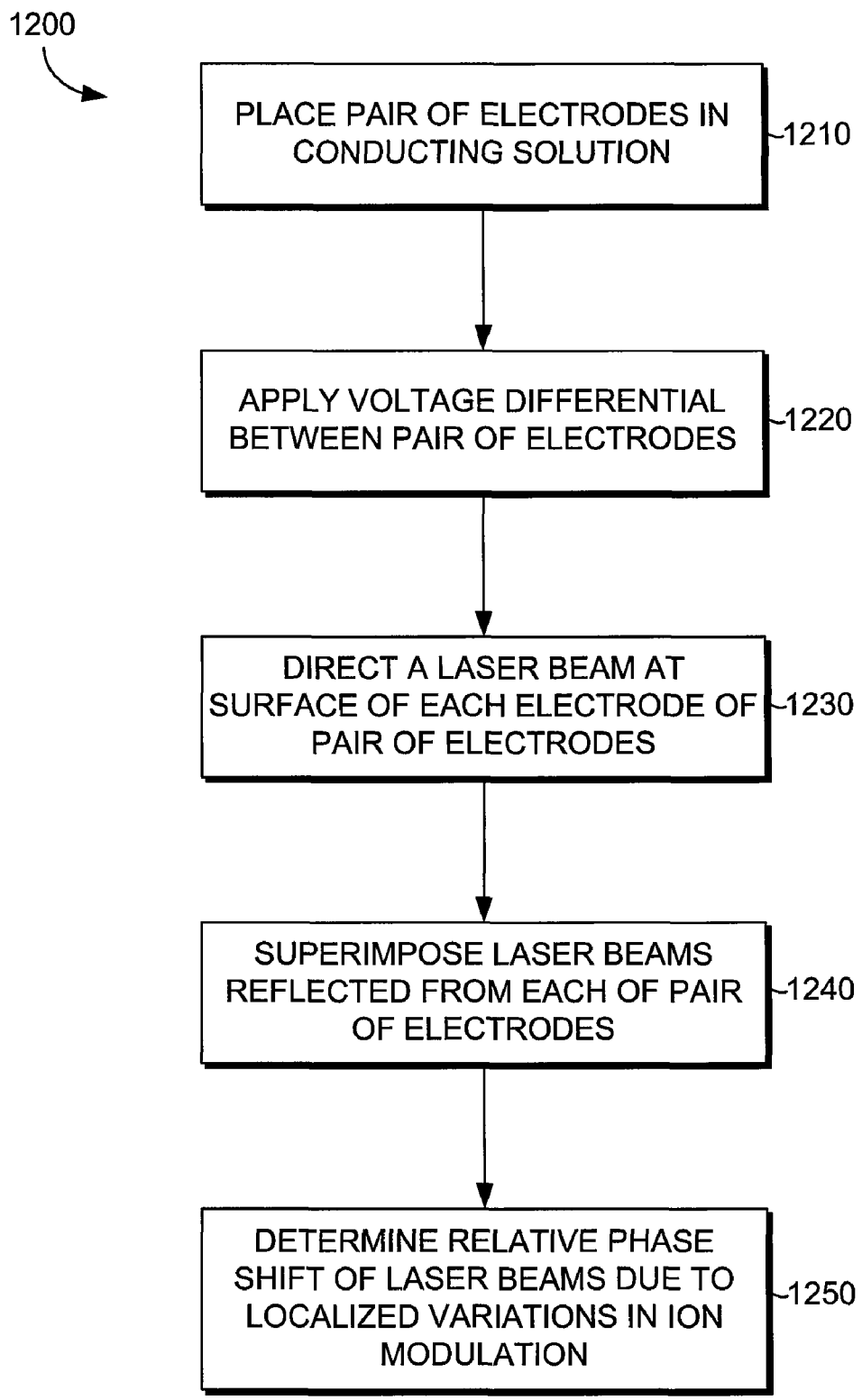
FIG. 12 illustrates a method in accordance with the present invention.

Referring now to FIG. 12, a method 1200 in accordance with the present invention is illustrated. In step 1210, a pair of electrodes is placed in a conducting solution. The conducting solution may contain ions that may conduct an electric current through the solution. A vessel or other container may contain the conducting solution and electrodes. One electrode of the pair of electrodes may comprise a reference electrode, and the other electrode of the pair of electrodes may comprise a working electrode. In step 1220, a voltage differential may be applied between the pair of electrodes. The voltage differential applied may be constant, time varying, or a constant differential with an additional time varying component. The voltage differential may be applied by grounding one electrode, such as the reference electrode, and applying a voltage to the other electrode, such as the working electrode. One of skill in the art will appreciate that the application of a voltage differential between the pair of electrodes will cause a current to move between the electrodes through the conducting solution. In step 1230, a laser beam may be directed at the surface of each electrode of the pair of electrodes. For example, a reference laser beam may be directed to the surface of the reference electrode, and a signal laser beam may be directed to the surface of the working electrode. As a result of directing a laser beam at the surface of each electrode of the pair of electrodes in step 1230, the laser beams will be reflected from the surface of each electrode of the pair of electrodes. In step 1240, the reflected laser beams from each pair of electrodes are superimposed. The superimposition of the reflected laser beam in step 1240 permit interferometry to be performed on the reflected laser beams to measure relative path length differences of the two beams, based upon any relative phase shift between the two laser beams. In step 1250, such a relative phase shift of the laser beams are determined. The relative phase shift determined in step 1250 will be due to localized variations in ion modulation at the surface of each electrode in a pair of electrodes.

Figure 13:
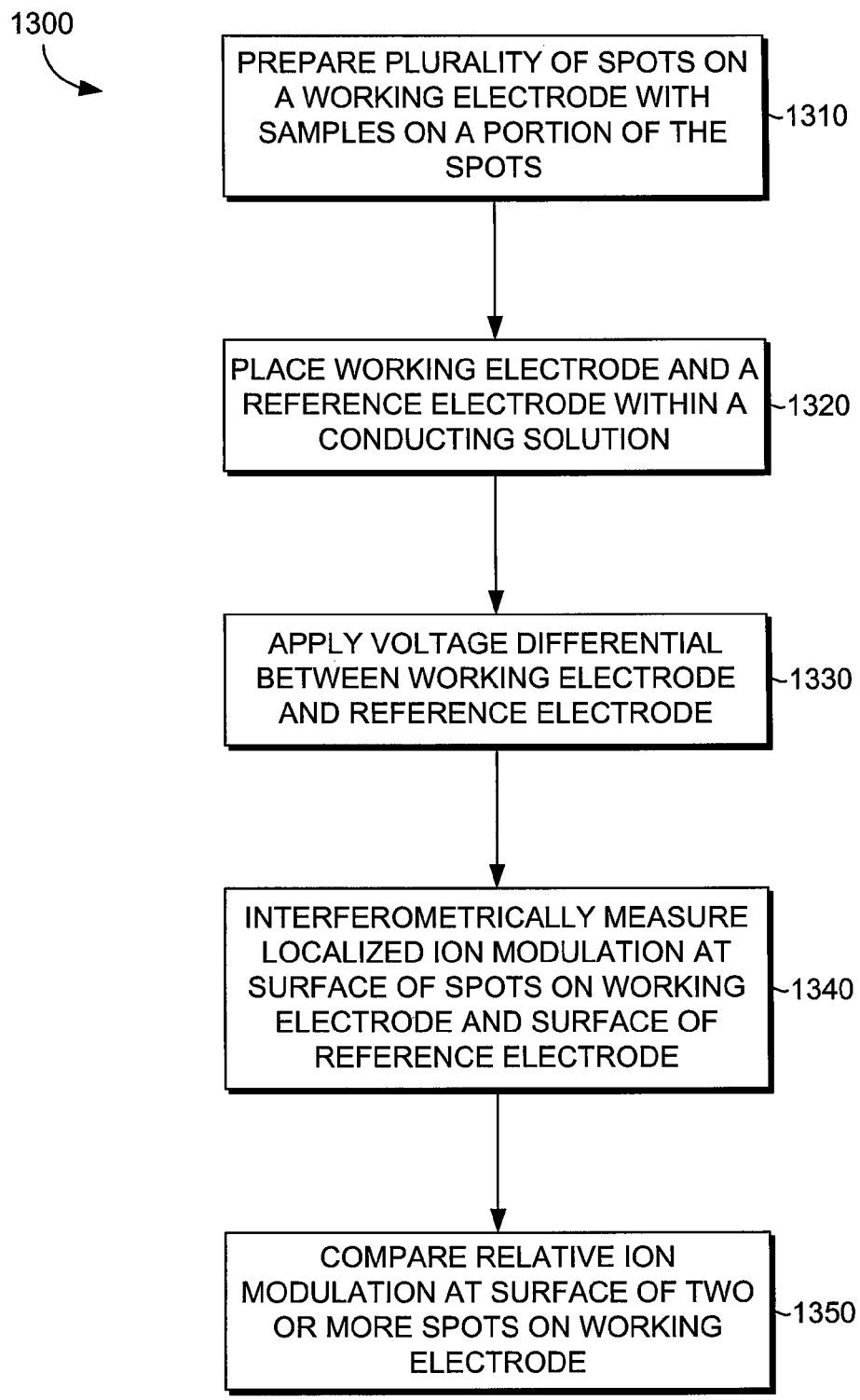
FIG. 13 illustrates a further method in accordance with the present invention.

Referring now to FIG. 13, a further method 1300 in accordance with the present invention is illustrated. In step 1310 a plurality of spots on a working electrode may be prepared, with samples on a portion of the plurality of spots. The plurality of spots may, for example, comprise a matrix of spots on the surface of the working electrode, although any arrangement and/or any number of spots may be used within the scope of the present invention. The samples placed on a portion of the plurality of spots may comprise the same or differing materials. The portion of spots prepared with some type of sample may be the entire plurality of spots on the working electrode or a subset of the plurality of spots on the working electrode. In step 1320, the working electrode and a reference electrode are placed within a conducting solution. The conducting solution may contain ions to permit the conduction of an electric current through the solution. The working electrode, reference electrode, and conducting solution may be contained within a vessel. In step 1330, a voltage differential may be applied between the working electrode and the reference electrode. For example, the reference electrode may be electrically grounded and varying or constant voltages applied to the working electrode. The voltage differential between the working electrode and the reference electrode may be constant, time varying, or constant with a time varying component. In step 1340, localized ion modulation may be interferometrically measured at the surface of spots on the working electrode relative to the surface of the reference electrode. Step 1340 may be performed for all or part of the spots on the surface of the working electrode. Step 1340 may be performed sequentially for spots on the surface of the working electrode in a process similar to the scanning of a compact disc by a laser. However, more than one laser may be applied to spots on the working electrode simultaneously, allowing the simultaneous measurement of ion modulation at multiple spots on the surface of a working electrode. In step 1350, the relative ion modulation at the surface of two or more spots on the working electrode may be compared. Step 1350 may utilize two or more ion modulation measurements taken solely at spots on the surface of the working electrode, but a comparison of ion modulation at the surface of any given spot on the surface of the working electrode relative to the ion modulation at the surface of the reference electrode can provide an absolute measurement of ion modulation at the surface of the working electrode. Therefore, it may be desirable in some applications to measure each of a plurality of spots on the working electrode relative to the reference electrode, and then compare the absolute ion modulations at each of the spots on the working electrode.

Figure 14:
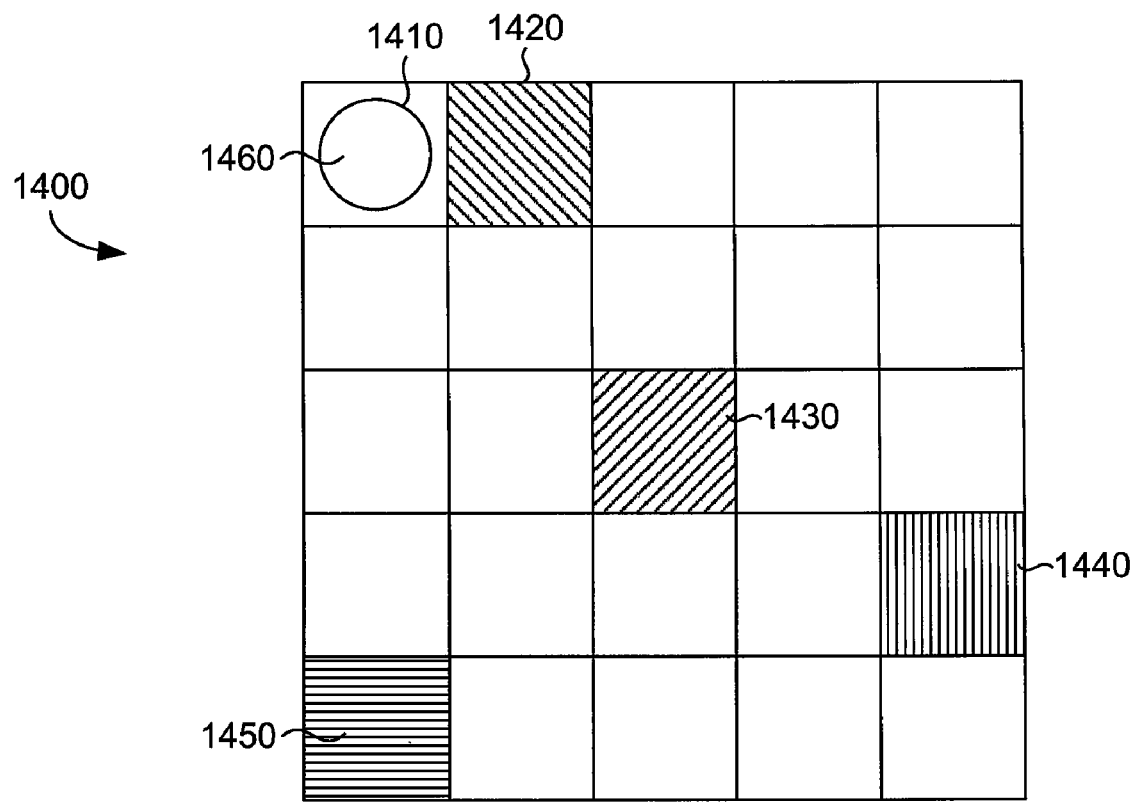
FIG. 14 illustrates a working electrode having a plurality of spots for testing samples in accordance with the present invention.

Referring now to FIG. 14, the surface 1400 of a working electrode divided into a plurality of spots in accordance with the present invention is illustrated. While FIG. 14 illustrates a 5×5 matrix with a total of 25 spots, one of ordinary skill in the art will appreciate that more or fewer spots on the surface of a working electrode may be used in accordance with the present invention, and will further appreciate that any arrangement of spots may be utilized without departing from the scope of the present invention. As illustrated in FIG. 14, a first spot 1410 does not include any sample. A laser beam 1460 is incident upon first spot 1410 at the point in time illustrated in FIG. 14. A second spot 1420 contains a first sample. A third spot 1430 contains a second sample. A fourth spot 1440 contains a third sample. A fifth spot 1450 contains a fourth sample. Differences between the samples applied to the various spots may result in differing ion modulations at the surface of first spot 1410 (which contains no sample), second spot 1420 (which contains a first sample), third spot 1430 (which contains a second sample), fourth spot 1440 (which contains a third sample), and fifth spot 1450 (which contains a fourth sample). After the point-in-time illustrated in FIG. 14, laser beam 1460 may move to another spot, such as second spot 1420. One of skill in the art will appreciate, however, that additional laser beams beyond laser beam 1460 illustrated may be utilized simultaneously without departing from the scope of the present invention. One of skill in the art will further appreciate that working electrode, the surface 1400 of which is illustrated in FIG. 14, may be used in conjunction with a reference electrode (no illustrated), a conducting solution (not illustrated), an interferometer (not illustrated) and other additional components as described herein.

Figure 8:
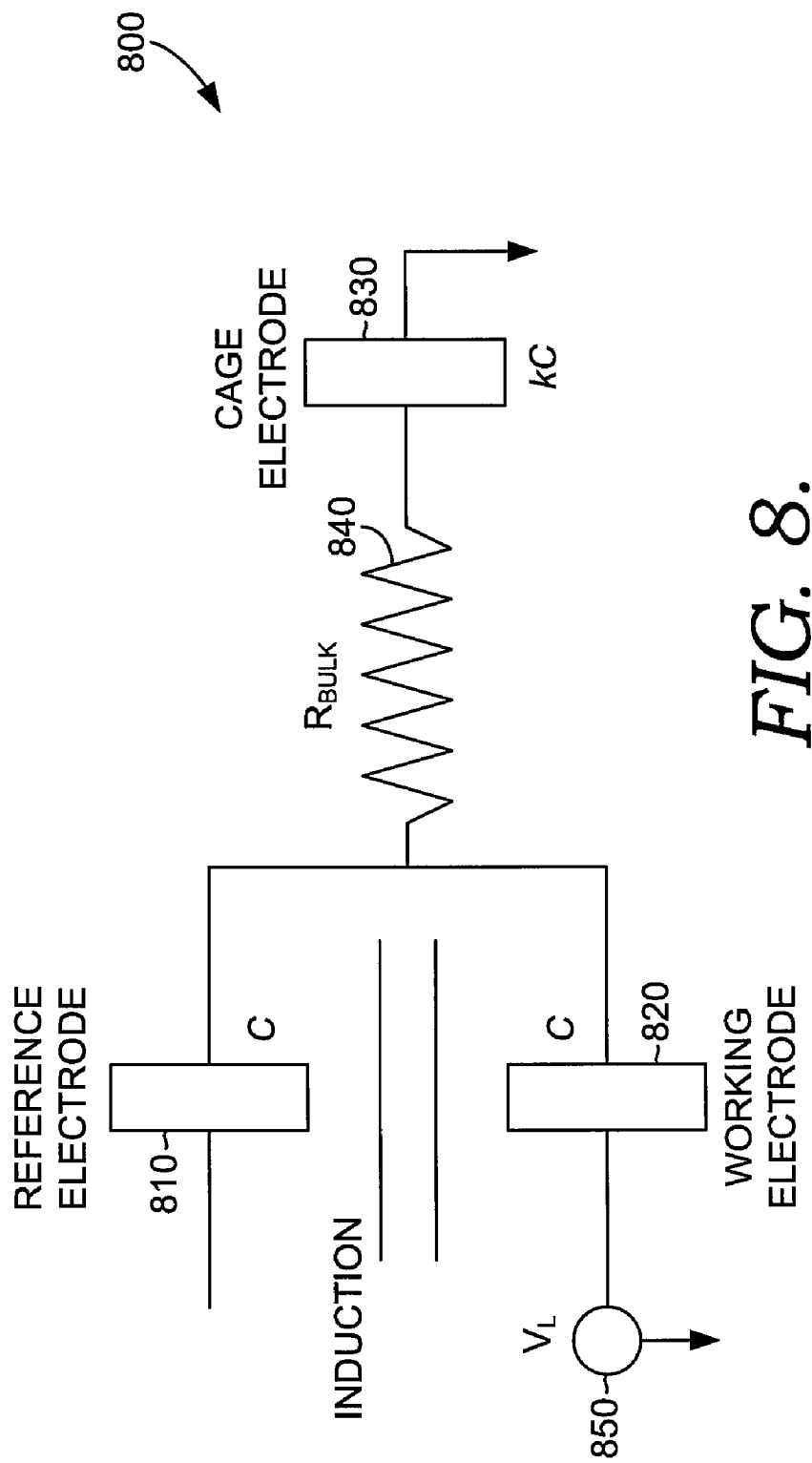
FIG. 8 illustrates a representative circuit in accordance with the present invention.

FIG. 8 illustrates an equivalent electrical circuit that may alternatively be used to model the system illustrated in FIG. 2, with the interfacial layers shown as capacitors and the bulk solutions shown as a pure resistor. The electrical circuit comprises reference electrode 810, working electrode 820, cage electrode 830, resistor 840, and applied potential 850. As there are no Faradic processes, the EDL is modeled as a pure capacitor of capacitance C. As the EDL capacitance is proportional to the electrodes' surface area, the relative impedances of working electrode 820 and cage electrode 830 are scaled by k=(area of cage electrode/area of working electrode). The external applied AC potential is $V_L e^{j\omega t}$ on working electrode 820 and the induced AC potential on reference electrode 810 is $V_R e^{j(\omega t + \Phi)}$, where $\omega$ is the AC potential frequency, and $\Phi$ is the phase difference between the reference and working electrode. Reference electrode 810 potential is with respect to ground and may be measured with a voltmeter, such as vector voltmeter 230 shown in FIG. 2. The amplitude of the AC potential applied on working electrode 820 ($V_L$) may, for example, range from $V_L$=0.1 to 5 V. Cage electrode 830 may be grounded.

When working electrode 820 has an applied potential of $+V_L$ and reference electrode 810 has an induced potential of $+V_R$ induced by $V_L$, the cations will be discharged from these electrodes and accumulate at cage electrode 830. As no Faradic process occurs in the system, this will lead to total charge conservation. As the potential reverses, the cation charging will reverse. Thus, under steady-state AC potential, the AC current in the bulk will not lead to any charge accumulation. In other words, no modulation of charge in the bulk will occur. The charge accumulation will occur only at the electrode interfaces. If the power supply and ground are swapped between the working electrode 820 and cage electrode 830, the phase between the applied potential and $(A-B)_{AC}$ is exactly inverted by a phase angle of 180 degrees. One of skill in the art may understand that this implies that the cation discharging is now charging at the working electrode 820 and reference electrode 810 (with respect to the applied potential). As cage electrode 830 is not in the beam path, the dynamics of ion accumulation at cage electrode 830 does not contribute to path length modulation measured by $(A-B)_{AC}$. The total measured current through the electrochemical cell and applied AC potential is nominally in phase (with no higher harmonics), implying that the ionic current is essentially determined by the (ohmic) resistance of the bulk.

Figure 9A:
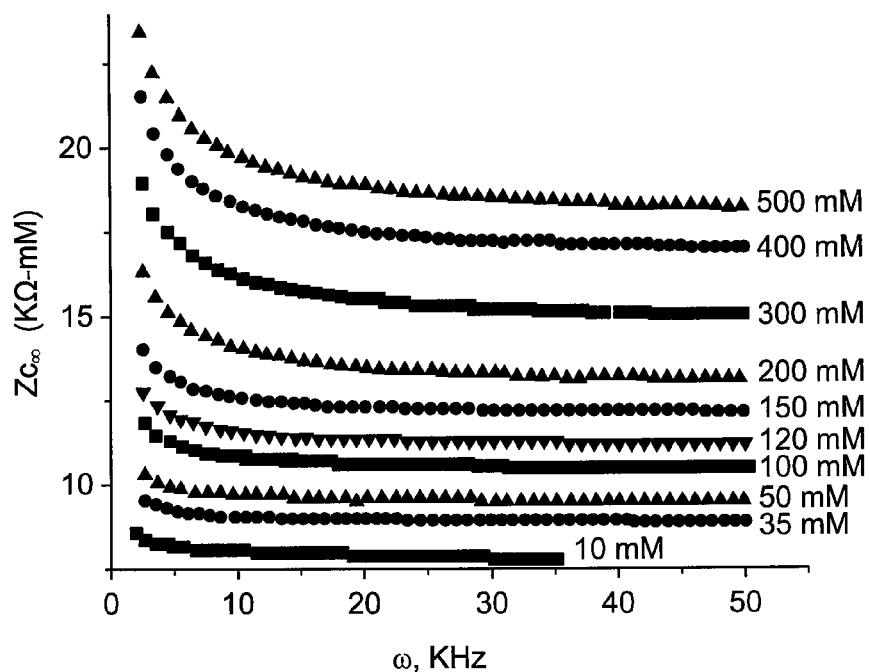
FIGS. 9A through 11B show further measurements taken in accordance with the present invention.

Referring again to FIG. 8, the current measured between cage electrode 830 and working electrode 820 can be used to calculate the total system impedance, $Z=V_L/I$. FIG. 9A illustrates a weak frequency dependence of impedance in the low-frequency regime by plotting the total system impedance as a function of frequency, $\omega$. This may be due to the contribution from the interface capacitance that will become progressively less as frequency increases. The curves are scaled by concentration to simply adjust their range on a single plot. Consistent with $C\sim 1/\zeta\sim c_\infty^{0.5}$, the capacitive effect is larger at higher concentration. At high frequency, the impedance plateaus, corresponding to the bulk resistance, $R_{bulk}$. Although not shown, one of ordinary skill in the art can appreciate that $R_{bulk}$ may be estimated from extrapolating the $1/\omega$ versus $Z$ plot to $1/\omega \to 0$ and is within 3% of the values obtained from the plot in FIG. 9A.

Figure 9B:
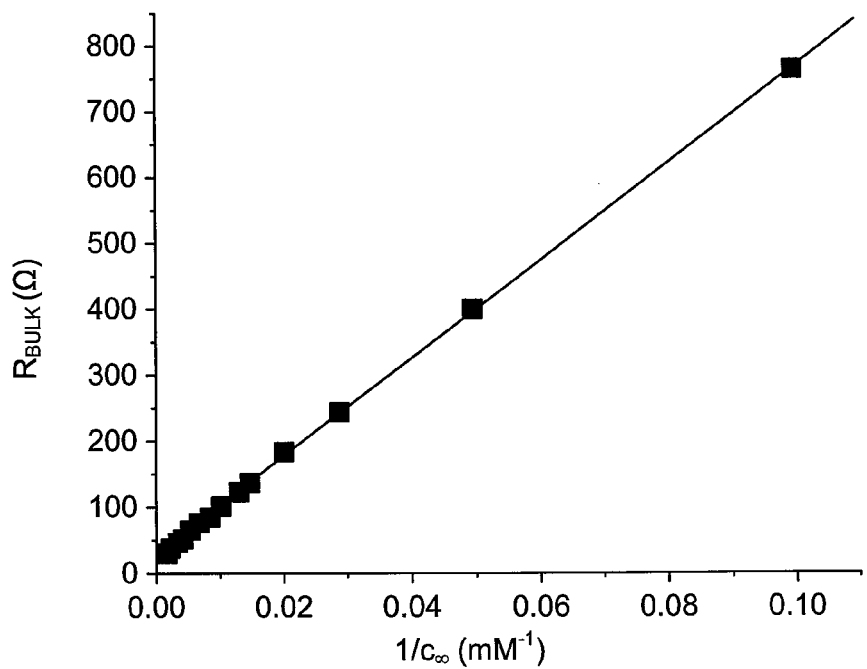

FIG. 9B illustrates that $R_{bulk}$ is linear with respect to $1/c_\infty$, as expected from ionic conductivity. Thus the equivalent circuit diagram in FIG. 8 is reasonable. From the equivalent diagram in FIG. 8 the voltage drop in the EDL, given by $V_L-IR_{bulk}$, is 10 to 100 mV where $V_T=1V$ over a concentration range of 10 to 500 mM and for a frequency up to 30 kHz. This corresponds to a potential of about 35kT/e at the edge of the EDL, which is well above the thermal energy of the ions. At higher frequency, the drop is smaller.

With continued reference to FIG. 8, the optical response may be considered. From equation 2 the measured absolute path length modulation is proportional to the charge modulation of the anion in the EDL of working electrode 820. Because the effect from reference electrode 810 is accounted for in equation 1, the electric circuit analysis utilizes working electrode 820 modulating at $V_T \exp(j\omega t)$ and cage electrode 830 is grounded. The charge accumulation in the capacitor C is calculated to give the path length modulation with use of equation 1:

$$\tan\theta_A = -\omega R_{bulk} C_{eq} \qquad \text{(Equation 4a)}$$

$$\Delta_A = \left(\frac{dn}{dc}\right)_- \frac{Q_-\zeta/e}{N_A} \sim \left(\frac{dn}{dc}\right)_- \frac{V_T C_{eq}}{[1+\omega^2(R_{bulk}C_{eq})^2]^{0.5}} \qquad \text{(Equation 4b)}$$

Where Q is negative charge per unit volume and $C_{eq}=[k/(1+k)]C$. For the present example configuration, $k\sim 10$, which corresponds to $C_{eq}\sim C$ within 10 percent. As electrical measurement related to $C_{eq}$ and $R_{bulk}$ is based on the total charge and the optical measurement related to $\Delta_A$ is only dependent on the negative charge, Q, (i.e., Cl$^-$), the two measurements are proportional but not equal. Furthermore, optical measurement corresponds to local ion motion in the area illuminated by the laser beam while the electrical measurement is averaged over the whole electrode. As there is spot-to-spot variation, the correspondence between the left-hand and right-hand sides of the proportionality in equation 4b is only qualitative. The ability to probe "local" dynamics away from electrode edge in the interferometric measurements is a distinct advantage over the electrical measurement as it avoids complications due to fringe fields and edge effects. As a result, the electrical design of the cell for optical measurements is simplified significantly.

Figure 10A:
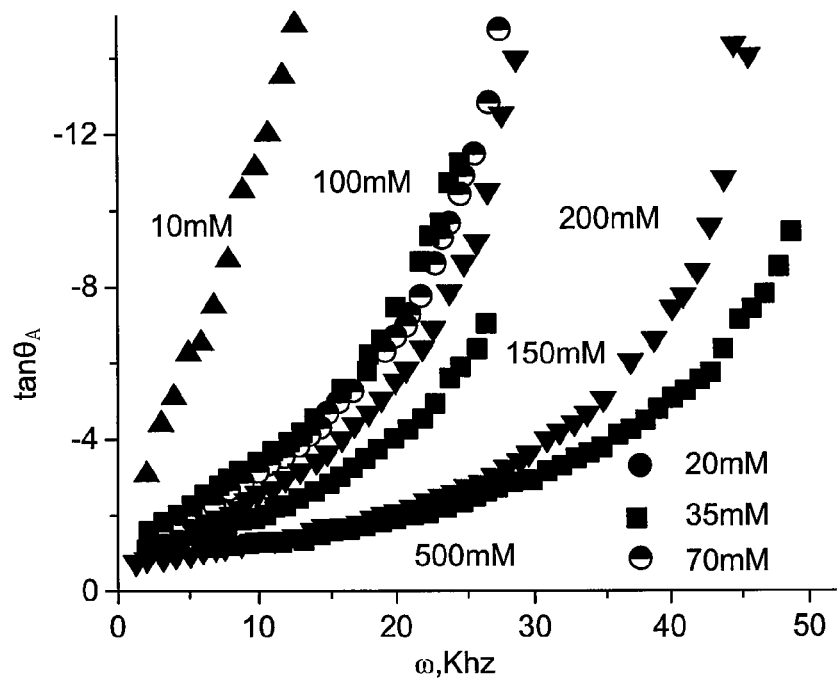
Figure 10B:
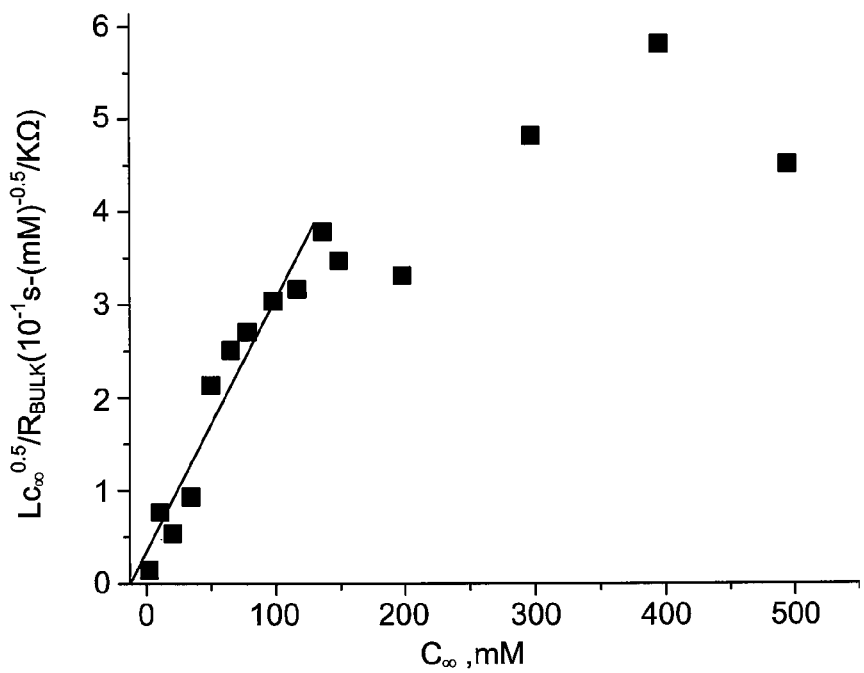

FIG. 10A shows the phase angle, $\tan\theta_A$, as a function of frequency, $\omega$. Owing to the linearity between $|V_T|$ and $\Delta_A$, all the curves are normalized for $|V_T|=1V$. Consistent with equation 4a, at low frequency, $\omega$ below 20 kHz, $\omega$ versus $\tan\theta_A$ is a straight line with slope L. Furthermore, because $R_{bulk}\sim c_\infty^{-1}$ and $C\sim c_\infty^{0.5}$ (assuming EDL is a parallel plate capacitor with thickness proportional to the EDL thickness, $\zeta$), one of skill in the art may appreciate that the slope in FIG. 10A should change as $c_\infty^{0.5}$. The slope, L, decreases as bulk solution concentration, $c_\infty$, increases. FIG. 10B shows a linear correlation for $(Lc_\infty^{0.5})/R_{bulk}$ as a function of the solution concentration, $c_\infty$, up to 150 mM, consistent with equation 4a. However, extrapolating the linear response of the phase in the low-frequency region, i.e., as $\omega\to 0$, $\theta_A$ does not tend toward 180 degrees as predicted by equation 4a. One of skill in the art may appreciate that the deviation from the expected 180 degrees is attributed to the effects of dynamics in the diffusion layer that may become significant as frequency decreases beyond 1 kHz because h is approximately $\sqrt{D/\omega}$. Measurement below 1 kHz is not possible in present exemplary configuration due to electrolysis of water that leads to visible etching of the electrode.

Figure 11A:
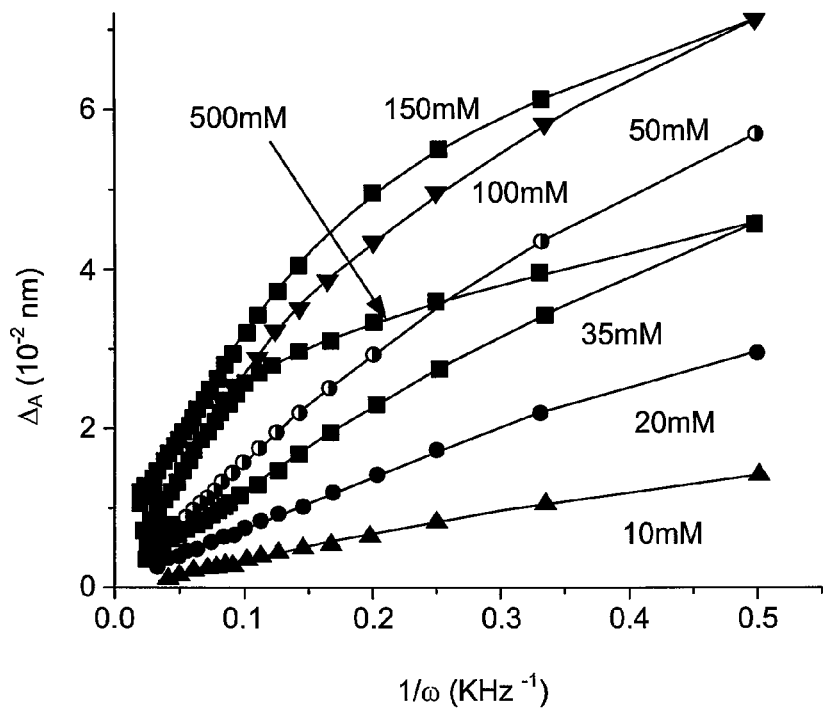
Figure 11B:
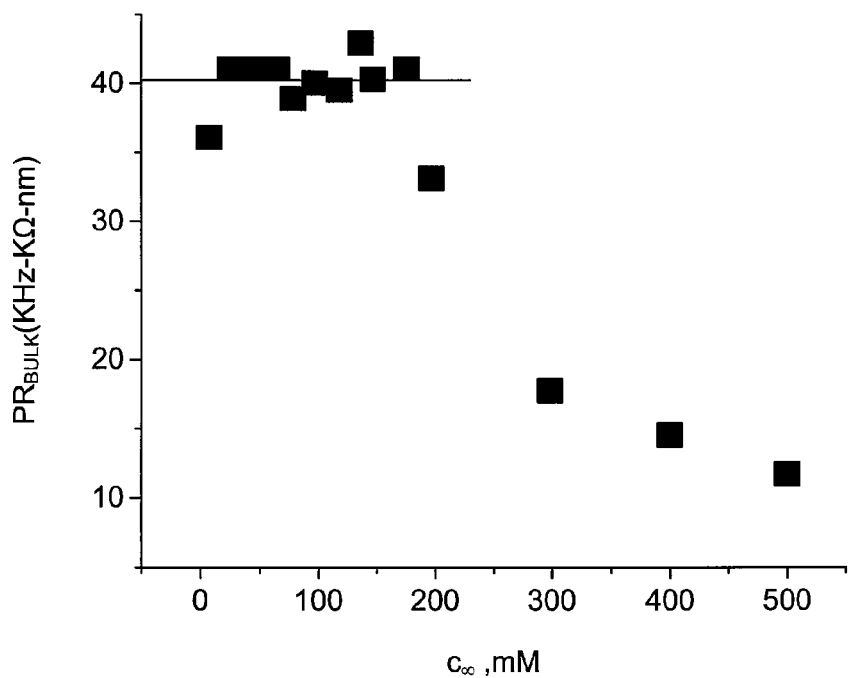

In FIG. 11A absolute modulation, $\Delta_A$, is measured as function of applied frequency $\omega$ as a function of $1/\omega$. All the curves are normalized to $|V_T|=1V$. Consistent with equation 4b, at high frequencies, the curve is linear with a slope, P, that increases with solution concentration, $c_\infty$. The frequency response for concentrations greater than 150 mM changes significantly as seen by the curve for 500 mM in FIG. 11A. Additionally, according to equation 4b, $PR_{bulk}$ should be a constant, independent of concentration. FIG. 11B illustrates that $PR_{bulk}$ is reasonably constant, within 10 percent, for concentrations below 180 mM. The system is linear for concentrations up to 500 mM, but deviates from the classical RC model.

The dynamics examined herein are primarily due to charge modulation in the EDL. The dynamics are highly linear up to an external electrode potential of about 2 V and bulk concentration of the ions in the solution up to about 0.5 M. The RC circuit model for the whole electrochemical system semi-quantitatively explains the frequency response of the ion dynamics at the interface. The RC model reasonably explains the trends for NaCl concentrations below 150 mM for $\omega>1$ kHz.

The optical method has two advantages. First, as shown in FIGS. 9A and 11A, the change in current with respect to frequency is at most 30% at high concentration in contrast to a ten-fold change in $\Delta$ as a function of $\omega$ for the optical measurement. This indicates that the capacitive effect of EDL is eclipsed by the bulk effect in the electrical measurement while optical measurement observes the charge indirectly. Second, in the optical measurement the local ion dynamics is measured as opposed to integrated current over the whole electrode in the electrical method. The local measurement allows for simpler electrochemical cell design where the electrode edge effects and fringe fields can be avoided by simply choosing a "sweet" spot on the electrode. Furthermore, the local probing with the optical technique can be extended to combinatorial measurements and microelectrode geometries.

Many different arrangements of the various components depicted, as well as components not shown, are possible without departing from the spirit and scope of the present invention. For example, the displaced beams may be focused on live and reference electrodes that are over 1 mm apart to avoid induction effects, which may lead to a more direct measurement where $\Delta_0$ and $\Delta_{90}$ are in-phase and out-of-phase components of $\Delta$ are obtained from the lock-in-amplifier (i.e., $\Delta_A=\Delta$). Furthermore, the design of the differential interferometer may be modified from the Nomarski type system described above to a heterodyne differential interferometer that is well known to one of skill in the art. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. A system to measure electrochemical processes, the system comprising:
   a pair of electrodes;
   a conductive solution containing ions that at least partially covers the pair of electrodes;
   a vessel that contains the pair of electrodes and the conductive solution;
   a voltage source electrically connected to the pair of electrodes to create a voltage differential between the pair of electrodes; and
   an interferometer that generates a signal laser beam incident on a first spot of one electrode of the pair of electrodes and a reference laser beam incident on a second spot of the other electrode of the pair of electrodes such that the signal laser beam and the reference laser beam are reflected from each of the pair of electrodes and superimposed to generate a signal indicative of the relative phase shift of the laser beam incident on each of the pair of the electrodes, the phase shift occurring due to differences in path lengths because of a difference in the refractive index of the conductive solution at the first spot and the refractive index of the conductive solution at the second spot, the difference in the refractive index at the first spot and the refractive index at the second spot being due to localized differences in ion concentrations in the conductive solution.

2. The system of claim 1, wherein the pair of electrodes comprise Au electrodes.

3. The system of claim 1, wherein the surface of at least one electrode of the pair of electrodes is divided into a plurality of spots on the electrode surface, one of the laser beams being sequentially incident upon each of the plurality of spots.

4. The system of claim 3, wherein the plurality of spots on the electrode surface comprises a 100×100 matrix.

5. The system of claim 3, wherein each spot is approximately 20 microns by 20 microns.

6. The system of claim 1, wherein the solution vessel comprises an Au plated Ti chamber.

7. A method for measuring the modulation of ions in a conducting solution, the method comprising:
   applying a voltage differential between a pair of electrodes comprising a reference electrode and a working electrode, both of the electrodes being at least partially in contact with a conducting solution;
   directing a signal laser beam onto the working electrode and directing a reference laser beam onto the reference electrode, the signal laser beam and the reference laser beam being in phase and traversing identical distances but for refractive effects of the conducting solution;
   superimposing the signal laser beam reflected from the working electrode and the reference laser beam reflected from the reference electrode; and
   generating a signal based upon the superimposed reflected signal laser beam and the reflected reference laser beam, the generated signal corresponding the phase difference of the signal laser beam and the reference laser beam due to the different path lengths of the reflected laser beams, the path lengths varying due to localized variations in the refractive index of the conducting solution due to localized modulation of ions at the surface of the reference electrode relative to the localized modulation of ions at the surface of the working electrode.

8. The method of claim 7, further comprising preparing at least two spots on the surface of the working electrode by applying at different materials different spots; and
   wherein directing the signal laser beam onto the working electrode further comprises sequentially directing the signal laser beam onto each of the at least two spots on the surface of the working electrode.

9. The method of claim 8, wherein generating a signal based upon the superimposed reflected signal laser beam and the reflected reference laser beam, the generated signal corresponding the phase difference of the signal laser beam and the reference laser beam due to the different path lengths of the reflected laser beams, the path lengths varying due to localized variations in the refractive index of the conducting solution due to localized modulation of ions at the surface of the reference electrode relative to the localized modulation of ions at the surface of the working electrode further comprises generating a signal for each of the at least two spots.

10. The method of claim 9, further comprising comparing the signals generated for each of the at least two spots to determine the relative localized modulation of ions at the surface of each of the at least two spots.

11. A method for measuring localized ion modulation at the surface of a plurality of spots on an electrode within a conducting solution, the method comprising:
   preparing a plurality of spots on a working electrode by placing differing materials on at least a first portion of the plurality of spots;
   placing a reference electrode and the working electrode at least partially within a solution containing ions that permits the solution to conduct an electrical current;
   applying a voltage differential between the reference electrode and the working electrode; and
   interferometrically measuring the localized ion modulation at the surface of at least a second portion of the spots on the working electrode relative to the localized ion modulation at the surface of the reference electrode.

12. The method of claim 11, wherein the second portion of the plurality of spots comprises the first portion of the plurality of spots.

13. The method of claim 12, wherein the first portion of the plurality of spots comprises the plurality of spots.

14. The method of claim 11, wherein the plurality of spots comprises a matrix of spots.

15. The method of claim 11, wherein interferometrically measuring the localized ion modulation at the surface of at least a second portion of the spots on the working electrode relative to the localized ion modulation at the surface of the reference electrode comprises measuring the localized ion modulation at the surface of at least a second portion of the spots sequentially.

16. The method of claim 11, wherein interferometrically measuring the localized ion modulation at the surface of at least a second portion of the spots on the working electrode relative to the localized ion modulation at the surface of the reference electrode comprises measuring the localized ion modulation at the surface of at least a second portion of the spots simultaneously.

17. The method of claim 11, wherein applying a voltage differential between the reference electrode and the working electrode comprises applying a time varying differential.

18. A localized ion concentration measurement device comprising:
- a reference electrode electrically having a planar surface connected to electrical ground;
- at least one working electrode having a planar surface;
- a voltage source electrically connected to the at least one working electrode;
- a plurality of reference spots on the planar surface of the at least one working electrode, at least a portion of the plurality of reference spots having a samples for analysis on the surface of the working electrode at that reference spot;
- a vessel containing a conducting fluid containing ions, the conducting fluid contained in the vessel covering the plurality of reference spots on the planar surface of the at least one working electrode and at least a portion of the planar surface of the reference electrode, such that an electrical current may flow between the reference electrode and the at least one working electrode through the conducting fluid in response to a voltage applied to the working electrode by the voltage source; and
- an interferometer that compares the refractive index of the conducting fluid at the plurality of reference spots on the planar surface of the at least one working electrode and the refractive index of the conducting fluid at a spot on the planar surface of the reference electrode.

* * * * *